Figure 1:
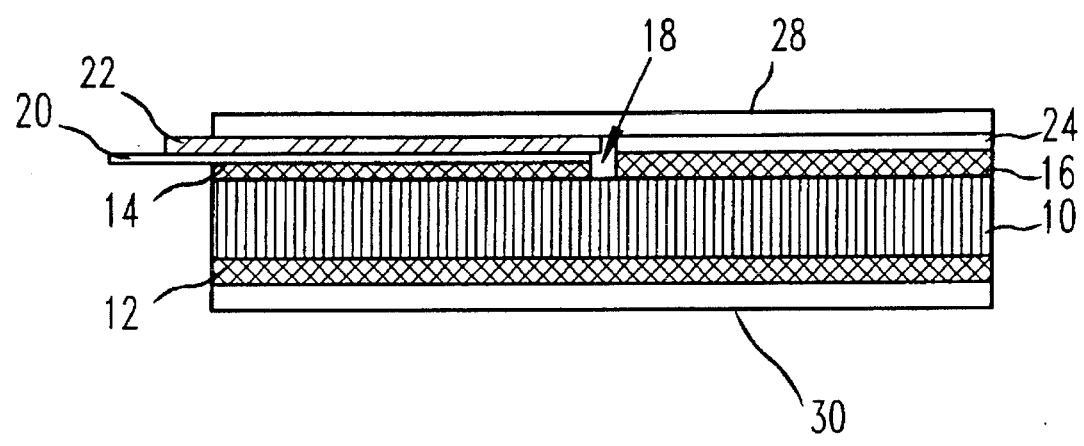

United States Patent [19]
Behl et al.

[11] Patent Number: 5,492,610
[45] Date of Patent: Feb. 20, 1996

[54] SOLID STATE ELECTROCHEMICAL CELL FOR PERFORMING ELECTRO-CHEMICAL MEASUREMENTS ON A SOLID ELECTROLYTE AT HIGH TEMPERATURES

[75] Inventors: Wishvender K. Behl, Ocean; Edward J. Plichta, Howell, both of N.J.

[73] Assignee: The United States of America as represented by the Secretary of the Army, Washington, D.C.

[21] Appl. No.: 324,846

[22] Filed: Oct. 18, 1994

[51] Int. Cl.$^6$ ................................................ G01N 27/26
[52] U.S. Cl. .................... 204/412; 204/421; 204/424; 204/426; 204/427; 429/191; 429/193; 429/218; 205/783.5
[58] Field of Search ............................ 204/412, 421, 204/424, 426, 427, 153.18; 429/191, 193, 218

[56] References Cited

U.S. PATENT DOCUMENTS 5,240,790  8/1993  Chua et al. ........................ 429/192

*Primary Examiner*—Bruce F. Bell
*Attorney, Agent, or Firm*—Michael Zelenka; Roy E. Gordon

[57] ABSTRACT

A solid state electrochemical cell is provided for performing electrochemical measurements on a solid electrolyte at high temperatures. The solid state electrochemical cell includes a noble metal working electrode, a lithium alloy reference electrode, and counter electrode, and a solid solution of lithium germanium oxide and lithium vanadium oxide as the solid electrolyte.

4 Claims, 1 Drawing Sheet

SOLID STATE ELECTROCHEMICAL CELL FOR PERFORMING ELECTRO-CHEMICAL MEASUREMENTS ON A SOLID ELECTROLYTE AT HIGH TEMPERATURES

GOVERNMENT INTEREST

The invention described herein may be manufactured, used, and licensed by or for the Government for governmental purposes without the payment to us of any royalties thereon.

FIELD OF INVENTION

The invention relates in general to solid state electrochemical cells and in particular to solid state electrochemical cells suitable for performing electrochemical measurements on a solid electrolyte at high temperatures.

BACKGROUND OF THE INVENTION

High temperature solid state electrochemical cells are being developed for pulse power applications using for example, highly conducting solid solutions of lithium germanium oxide ($Li_4GeO_4$) and lithium vanadium oxide ($Li_3VO_4$) as solid electrolytes. The solid solution that can be represented by the formula $Li_{3.6}Ge_{0.6}V_{0.4}O_4$ has a conductivity of about 0.08 S/cm at 300° C. and has been suggested as a lithium ion conducting solid electrolyte for solid state cells. However, a knowledge of the electrochemical stability range of these electrolytes, that is, potential limits between which the solid electrolyte is stable and does not undergo any electrochemical reduction or oxidation is required prior to their use as solid electrolytes in solid state cells.

SUMMARY OF THE INVENTION

The general object of this invention is to provide a solid state electrochemical cell for performing electrochemical measurements on a solid electrolyte at high temperatures. A more particular object of the invention is to provide such a cell where the solid electrolyte to be measured is a mixture of lithium germanium oxide and lithium vanadium oxide having the formula $Li_{3.6}Ge_{0.6}V_{0.4}O_4$.

It has now been found that the aforementioned objects can be attained by a solid state electrochemical cell having a three electrode arrangement including a working electrode, a reference electrode, a counter electrode, and a solid state electrolyte.

More particularly, according to the invention, the solid state electrochemical cell includes a sintered pellet electrolyte and a noble metal foil disc beneath the sintered pellet electrolyte. The noble metal foil disc serves as the working electrode. Pressed pellets of alloys are situated on top of the sintered pellet electrolyte and serve as the reference electrode and the counter electrode respectively. A small gap is provided in the middle so that there is no contact between the reference electrode and the counter electrode. A current collector is provided atop the reference electrode, and a spacer is provided atop the counter electrode. An insulator is provided on top of the current collector to isolate it from the spacer on top of the counter electrode. The cell stack is placed between plates that also act as current collectors for the counter electrode and the reference electrodes.

DESCRIPTION OF DRAWING AND THE PREFERRED EMBODIMENT

FIG. 1 is a schematic of the cell design of the invention. Referring to FIG. 1, an electrolyte, 10, is prepared as a 1 mm thick sintered pellet by pressing the powdered electrolyte at a pressure of 4500 kg in a 1.27 cm diameter steel die followed by sintering at 1000° C. between two platinum foil disks for three hours in air. The sintered pellet is cooled and the top platinum foil is removed. The platinum foil disk at the bottom, 12, has a surface area of 1.27 $cm^2$ and is used as the working electrode. A reference electrode 14 and a counter electrode, 16, are pressed pellets of lithium-aluminum alloy placed on top of the pressed electrolyte pellet, 10 as shown in FIG. 1 with a small gap, 18 in the middle so that there is no contact between the reference electrode, 14, and the counter electrode, 16. A molybdenum foil, 20, placed on top of the reference pellet electrode, 14, is used as a current collector, and a mica insulator, 22, is placed on top of the molybdenum foil or current collector, 20, to isolate it from a molybdenum spacer, 24, placed on top of the counter electrode, 16. The whole cell stack is placed between two molybdenum plates, 28 and 30, that also act as current collectors for the counter electrode, 16, and the reference electrode, 14. The cell stack is assembled in a dry box, sealed in a pyrex glass vessel using a spring loaded cell assembly and operated under a flowing argon atmosphere.

The three electrode solid state cell shown in FIG. 1 is used to determine the electrochemical stability range of the solid electrolyte, $Li_{3.6}Ge_{0.6}V_{0.4}O_4$, at 300° C. by performing cyclic voltammetric experiments. In these experiments, the potential of the platinum working electrode is varied as a function of time and measured against the lithium-alloy reference electrode. The current flowing between the platinum working electrode and lithium alloy counter electrode is then recorded and plotted as a function of the working electrode potential. The resulting current-voltage curve i.e., cyclic voltammogram shows anodic or positive currents at potentials where the oxidation of the electrolyte occurs and shows cathodic or negative currents at potential where the reduction of the solid electrolyte occurs. The cyclic voltammogram exhibits increasing cathodic currents at potentials below about 0.6 V due to the deposition of lithium metal on the platinum electrode resulting in the formation of a lithium-platinum alloy. At positive potentials, the cyclic voltammogram does not exhibit any anodic currents up to a potential of about 4.5 V indicating the absence of any oxidation of the solid electrolyte. Thus, the solid electrolyte is electrochemically stable between the voltage limits of lithium metal deposition on the cathodic side and up to at least 4.5 V on the anodic side and can be used as a lithium ion conducting electrolyte in high temperature solid state cells of the type $Li-Al/Li_{3.6}Ge_{0.6}V_{0.4}O_4/TiS_2$. The cell is cycled between the voltage limits of 2.3 V to 0 V at 300° C. during charge-discharge cycles that are well within the electrochemical stability range of the solid electrolyte.

The invention is important in that in order to make any electrochemical measurements in solid state cells, a three electrode system is required. The problem of using a reference electrode in a solid state cell is made more difficult because in a standard liquid cell, the reference electrode can be easily introduced into the cell by dipping the reference electrode into the electrolyte. Such an arrangement is not feasible when using a solid electrolyte.

In the invention, it is also necessary that the counter electrode be the same size or greater in size than the reference electrode. The reference electrode material is chosen so that one of the components of the reference electrode is common to the cation of the electrolyte and forms a reversible metal-metal ion couple in contact with the electrolyte.

The working electrode is a material that is chemically stable in reference to the electrolyte. It can be any of the noble metals.

We wish it to be understood that we do not desire to be limited to the exact details of construction shown and described for obvious modification will occur to a person skilled in the art.

What is claimed is:

1. A three electrode solid state electro-chemical cell including a working electrode, a reference electrode, a counter electrode, and a solid state electrolyte for performing electrochemical measurements on the solid electrolyte at temperatures of about 30° C. wherein the reference electrode and counter electrode is an alloy of lithium, the working electrode is a noble metal, and the solid electrolyte is a solid solution of lithium germaniumoxide and lithium vanadium oxide.

2. A three electrode solid state electrochemical cell including a working electrode, a reference electrode, a counter electrode, and a solid state electrolyte for performing electrochemical measurements on the solid electrolyte at temperatures of about 300° C. and wherein the solid electrolyte is a solid solution of lithium germanium oxide and lithium vanadium oxide.

3. A three electrode solid state electrochemical cell including a working electrode, a reference electrode, a counter electrode, and a solid state electrolyte for performing electrochemical measurements on the solid electrolyte at temperatures of about 300° C. and wherein the solid solution of lithium germanium oxide and lithium vanadium oxide has the formula $Li_{3.6}Ge_{0.6}V_{0.4}O_4$.

4. A solid state cell including a three electrode arrangement of a platinum working electrode, a LiAl reference electrode, and a LiAl counter electrode for performing electrochemical measurements on a solid electrolyte, said solid state cell including a solid sintered pellet of $Li_{3.6}Ge_{0.6}V_{0.4}O_4$ as the solid electrolyte, a platinum foil disc beneath said solid electrolyte, said platinum foil disc serving as the working electrode, pressed pellets of LiAl alloy atop the sintered pellet electrolyte serving as the reference electrode and the counter electrode with a small gap in the middle so that there is no contact between the reference electrode and the counter electrode, a molybdenum foil atop the reference electrode as the current collector, a molybdenum spacer atop the counter electrode and a mica insulator atop the molybdenum current collector to isolate it from the molybdenum spacer atop the counter electrode, the cell stack being placed between molybdenum plates that also act as current collectors for the counter and reference electrodes.

* * * * *